United States Patent
Brunner

(10) Patent No.: US 7,972,579 B2
(45) Date of Patent: Jul. 5, 2011

(54) DEVICE FOR THE AUTOMATIC OPENING AND CLOSING OF REACTION VESSELS

(75) Inventor: Wolfgang Brunner, München (DE)

(73) Assignee: F. Hoffmann-La Roche AG, Basel (CH)

( * ) Notice: Subject to any disclaimer, the term of this patent is extended or adjusted under 35 U.S.C. 154(b) by 841 days.

(21) Appl. No.: 10/561,424

(22) PCT Filed: Jul. 1, 2004

(86) PCT No.: PCT/EP2004/007179
§ 371 (c)(1),
(2), (4) Date: Mar. 7, 2006

(87) PCT Pub. No.: WO2005/002728
PCT Pub. Date: Jan. 13, 2005

(65) Prior Publication Data
US 2007/0098597 A1   May 3, 2007

(30) Foreign Application Priority Data

Jul. 4, 2003 (DE) .............................. 203 10 332 U

(51) Int. Cl.
*B01L 3/00* (2006.01)
(52) U.S. Cl. .......... 422/560; 422/63; 422/561; 422/562; 422/563; 422/564; 422/565; 422/566; 435/809
(58) Field of Classification Search .................. 422/99, 422/104, 560–566, 63; 435/809
See application file for complete search history.

(56) References Cited

U.S. PATENT DOCUMENTS

| 4,674,340 | A | 6/1987 | Burt et al. ................... 73/862.23 |
| 4,868,105 | A | 9/1989 | Urdea et al. |
| 5,533,407 | A | 7/1996 | Besnier ....................... 73/864.25 |
| 5,635,352 | A | 6/1997 | Urdea et al. |
| 5,681,702 | A | 10/1997 | Collins et al. |
| 6,132,684 | A | 10/2000 | Marino ......................... 422/104 |
| 6,216,340 | B1 | 4/2001 | Fassbind et al. ................ 29/773 |
| 2003/0038071 | A1* | 2/2003 | Hansen et al. ................ 210/222 |
| 2003/0118487 | A1 | 6/2003 | Pressman et al. ............. 422/104 |
| 2004/0014443 | A1 | 1/2004 | Nakao et al. .................. 455/130 |

FOREIGN PATENT DOCUMENTS

| EP | 0225807 B1 | 10/1994 |
| EP | 06014143 | 8/2006 |
| JP | 10147398 A | 6/1998 |
| JP | 2002068376 A | 3/2002 |
| WO | 9926070 A2 | 5/1999 |
| WO | 9926070 A3 | 5/1999 |

* cited by examiner

*Primary Examiner* — Jill Warden
*Assistant Examiner* — Shogo Sasaki
(74) *Attorney, Agent, or Firm* — Charles M. Doyle; Vivien M. Banholze; M. Reza Savari

(57) ABSTRACT

The invention relates to a device for the automatic opening and closing of reaction vessels. It comprises a holding device for the non-rotatable holding of one or more reaction vessels, a gripper for the gripping of a lid for the reaction vessel, wherein the gripper has gripping jaws to take hold of the lid, and a holding arm with a rotating mechanism for rotatable holding of the gripper. The gripping jaws are arranged in such a way that, when the lid is inserted into the area between the gripping jaws, it is held by the latter through frictional contact, and the gripper has no active operating device for opening and closing the gripping jaws.

5 Claims, 7 Drawing Sheets

DEVICE FOR THE AUTOMATIC OPENING AND CLOSING OF REACTION VESSELS

BACKGROUND OF THE INVENTION

1. Field of the Invention

The invention relates to a device for the automatic opening and closing of reaction vessels. In particular, the invention relates to the automatic opening and closing of reaction vessels with lids which may be screwed on to the reaction vessels. The invention is meant to be suitable in particular for applications involving a robot for the conduct of chemical and/or biological reactions.

2. Description of the Related Art

There are known devices for the automatic opening and closing of reaction vessels which have a gripper which may be activated to grip a lid and is provided with a rotating mechanism so that the gripper may be used to screw the lid on to a reaction vessel and to unscrew it from a reaction vessel. The reaction vessels generally have a special shape, so that they engage positively in a suitable holding area in a holder. By this means, a non-rotatable placement of the reaction vessel is ensured.

Known from U.S. Pat. No. 6,216,340 B1 is a similar device in which the reaction vessels have vertical ribs in a specific zone, so that they can engage positively in a holding element. This ensures non-rotatable placement of the reaction vessels. The lid of these reaction vessels is made with two horizontal slits, arranged diametrically opposite one another in the upper section of the body of the lid. Each of these slits leads at one end to the top of the lid, so that a lid gripping mechanism may engage in the lids by means of a horizontal pin, and is able to exert the necessary torque on the lid in order to unscrew it from the reaction vessel. For this gripper it is advantageous that it is not provided with a special operating mechanism for active gripping of the lid, but instead is able to engage the lid only passively by engaging the pins in the slits. This facilitates integration into a robot, since in this way an additional control function may be omitted. The drawback of this device, however, is that only specially designed lids may be used. It is not therefore possible to use reaction vessels obtained by a customer and closed with a conventional lid in a production process with such a device for the automatic opening and closing of reaction vessels, without replacing the lid. This would entail replacing a conventional lid by a lid specially designed for this purpose. Moreover these special lids are expensive.

SUMMARY OF THE INVENTION

The invention is therefore based on the problem of creating a device for the automatic opening and closing of reaction vessels which is simple in design yet still able to grip conventional screw lids easily and reliably for the opening and closing of reaction vessels.

This problem is solved by a device with the features of claim 1.

The invention is also based on the problem of creating a device for the automatic opening and closing of reaction vessels which may be used for the reliable opening and closing of conventional reaction vessels, not specially designed, and with a screw lid.

This problem is solved by a device with the features of claim 6.

Advantageous developments of the invention are set out in the respective dependent claims.

The device according to the invention for the automatic opening and closing of reaction vessels comprises:
- a holding device for the non-rotatable holding of one or more reaction vessels
- a gripper for the gripping of a lid for the reaction vessel, wherein the gripper has gripping jaws to take hold of the lid, and
- a holding arm with a rotating mechanism, for rotatable holding of the gripper.

The solution according to claim 1 is distinguished by the fact that the gripping jaws are arranged in such a way that, when the lid is inserted into the area between the gripping jaws, it is held by the latter through frictional contact, and the gripper has no active operating device for opening and closing the gripping jaws.

The lid is therefore held substantially by means of the frictional contact between the gripping jaws and the lid. No additional adjusting mechanism for operating the gripping jaws is necessary, nor is any such mechanism provided. Nevertheless, conventional lids may be held by the gripper, without the lids requiring any special design for this purpose.

According to a preferred development of the invention, the gripping jaws have on their gripping surfaces one or more cutting webs running at right-angles to the direction of rotation. This cutting web has a sharp cutting edge which engages with the surface of the lid, thereby allowing the transmission of considerable torque from the gripper to the lid.

The solution according to claim 6 is distinguished by the fact that the holding device has three perforated plates, arranged one above the other, and with openings to hold the reaction vessels. Here the top and bottom perforated plates are arranged so as to be stationary, with the openings made in them flush with one another, and the middle perforated plate is designed to slide between a first position in which its openings are aligned with the openings of the top and bottom perforated plates, and a second position in which its openings are arranged somewhat out of alignment with the openings of the top and bottom perforated plates, so that a reaction vessel inserted in the openings of the perforated plates is clamped non-rotatably, and means of fixing the middle perforated plate in the second position are provided.

One or more reaction vessels may be inserted in suitable openings in the perforated plates, and clamped non-rotatably in the perforated plates by sliding the middle perforated plate into the second position, while the reaction vessels are suitably held by the fixing of the middle perforated plate in the second position.

In a preferred embodiment, each of the openings of the middle perforated plate contains a projection which extends into the interior of the opening and is located roughly in the section area between a centre line of the opening concerned running in the direction of sliding, and the edge of the opening. When the reaction vessels are clamped in the perforated plates, this projection is pressed against the wall of the perforated plate, thereby effecting a positive holding of the reaction vessels.

Preferably each opening of the top and/or bottom perforated plates contains corresponding projections which are arranged diametrically opposite to the projection of the middle perforated plate. This enhances the engagement by which the reaction vessels are held in the perforated plates.

A further advantage of the device according to the invention is derived from the combination of the
- holding of the lid by frictional contact and
- holding of the reaction vessels by clamping, since the clamping of the reaction vessels also prevents vertical movement of the reaction vessels, therefore preventing shifting of the reaction vessels when the gripper is pushed on to the lid or when the lid is removed from the reaction vessel. The clamping of the reaction vessels this fulfils two functions, namely the non-rotatable holding of the reaction vessels during screwing the lid on and off, and the absorption of forces during pushing on of the gripper, removal of the lid, or removal of the gripper after screwing on the lid.

Due to the holding by clamping of the reaction vessels, the frictional force applied when the gripper is pushed on to a lid is limited solely by the mechanical properties of the device used to move the gripper. The clamped hold thus permits the use of considerable frictional forces in pushing on the gripper.

BRIEF DESCRIPTION OF THE FIGURES

FIG. 4b shows a top view of the arrangement of FIG. 4a.

FIG. 4c shows a partial section of the arrangement of FIG. 4a.

FIG. 6b is a perspective view of the reaction vessel and lid of FIG. 6a.

DETAILED DESCRIPTION OF THE INVENTION

Figure 1:
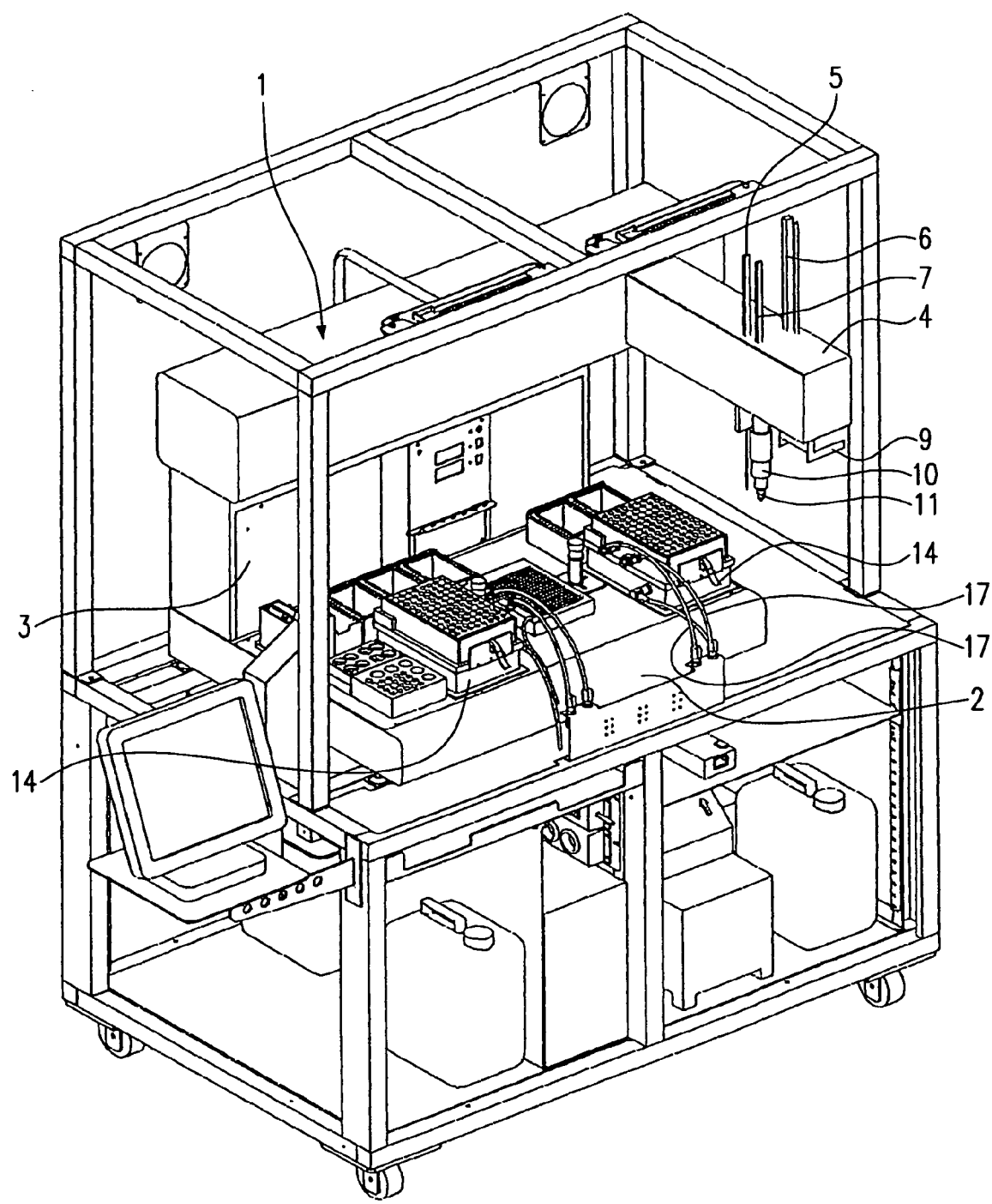
FIG. 1 illustrates a robot with a device according to the invention for the automatic opening and closing of reaction vessels.

The device according to the invention for the automatic opening and closing of reaction vessels is designed for use in a robot. Such a robot is shown schematically in FIG. 1. The robot 1 has a work platform 2, a rear wall 3 and a robot arm 4. The robot arm 4 may be traversed along a horizontal rail (not illustrated) on the upper edge area of the rear wall 3, so that it can sweep the entire area of the work platform 2. Arranged on the robot arm are three handling arms 5, 6, 7 which extend vertically. The handling arms are traversably mounted on rails (not shown) extending in the robot arm 4, so that they are able to traverse in the longitudinal direction of the robot arm 4. The handling arms are also able to traverse vertically. The handling arm 5 has a pipette tip for the pipetting of chemical and/or biological reagents. The handling arm 6 is provided with a fork-like gripping element 9, which may be used to handle microtitre plates. The handling arm 7 has at its lower end a rotating mechanism 10, to which is coupled a gripper 11 for gripping lids 12 for reaction vessels 13. The gripper 11 is explained in detail below.

Provided on the robot are various work stations, and a robot of this kind may be configured in various ways to meet the needs of the user. In the present embodiment, the work platform 2 is provided with two vibrator stations, each with a vibrator 14 on which is mounted a thermal block 15 for holding reaction vessels. The thermal block 15 is a rectangular body, made of material with good heat-conducting properties, in which are made passages for the flow of a tempered heat medium, for example silicone oil. On the upper side of the thermal block 15 are recesses in which the bottom section of the reaction vessels 13 is held positively, so that a good transfer of heat is possible between the thermal block 15 and the reaction vessels. Mounted on each of these vibrators 14 with a thermal block 15 is a rack 16 for handling a set of reaction vessels 13. This rack is explained in detail below.

The robot of this embodiment is provided for the direct quantification of the RNA of the hepatitis C virus (HCV RNA) in serum or plasma from HCV-infected persons by means of the VERSANT™ HCV RNA 3.0 test (bDNA) or for direct quantification of the RNA of the human immunodeficiency virus type I (HIV-I) in plasma from HIV-I-infected persons by means of the VERSANT™ HCV RNA 3.0 test (bDNA). In this context, reference is made to U.S. Pat. No. 4,868,105, U.S. Pat. No. 5,635,352 and U.S. Pat. No. 5,681,702 and to European patent EP 225 807 B. In the embodiment shown in FIG. 1, the robot 1 is mounted in a laboratory cabinet, with a unit for tempering and circulating the heat medium in the area beneath the robot. In this unit, the heat medium is fed to and removed from the thermal blocks by means of hoses 17.

The work platform 2 also has a container for disposable pipette tips and a container for used pipette tips. Other work stations may also be integrated with a robot 1 of this kind, for example a thermocycler. With regard to further configurations and the general structure of such a robot, reference is made to WO 99/26070, which is incorporated in the present description. Consequently, the opening defined by the gripping jaws 20, which is designed to hold a lid, may be adjusted within a certain range by means of the adjusting screws 23.

Figure 2B:
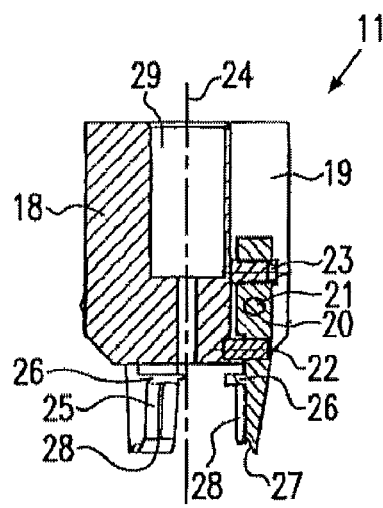
FIG. 2b shows the gripper of FIG. 2a in a sectional view.
Figure 2A:
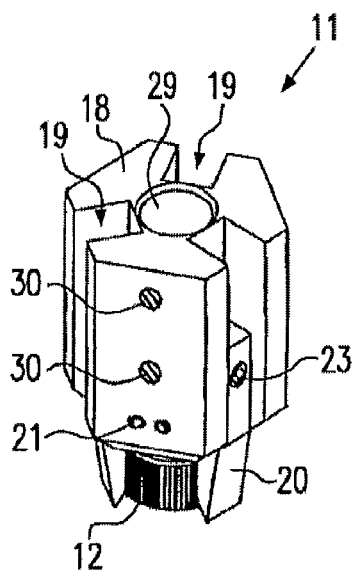
FIG. 2a is a perspective view of a gripper according to the invention.

FIGS. 2a and 2b show a first embodiment of the gripper 11 according to the invention. This gripper 11 has a roughly prism-shaped framework 18 with a regular hexagonal base and a corresponding upper surface. Made in the framework 18 on alternating side walls are three vertical slots 19. Each slot 19 contains a gripping jaw 20, which extends a short distance downwards from the framework 18. A shaft 21 passes through each of the gripping jaws 20 and is fastened to the framework 18.

Located between each of the gripping jaws 20 and the framework 18, in the area beneath the shafts 21, is a spring element 22, so that the lower ends of the gripping jaws 20 are pressed outwards. Above the shafts 21, each of the gripping jaws 20 contains a tapped hole, into which is screwed an adjusting screw 23, by means of which the distance between the bottom end of the respective gripping jaw 20 and a vertical axis of symmetry 24 may be adjusted.

In the area which extends below the framework 18, each gripping jaw 20 has a gripping surface 25 facing towards the axis of symmetry 24 of the gripper 11. Each gripping surface 25 is bounded at the top by a horizontal stop web 26. Adjoining the lower edge area of the gripping surface 25 is an insertion slope 27 running downwards and radially outwards.

Figure 6A:
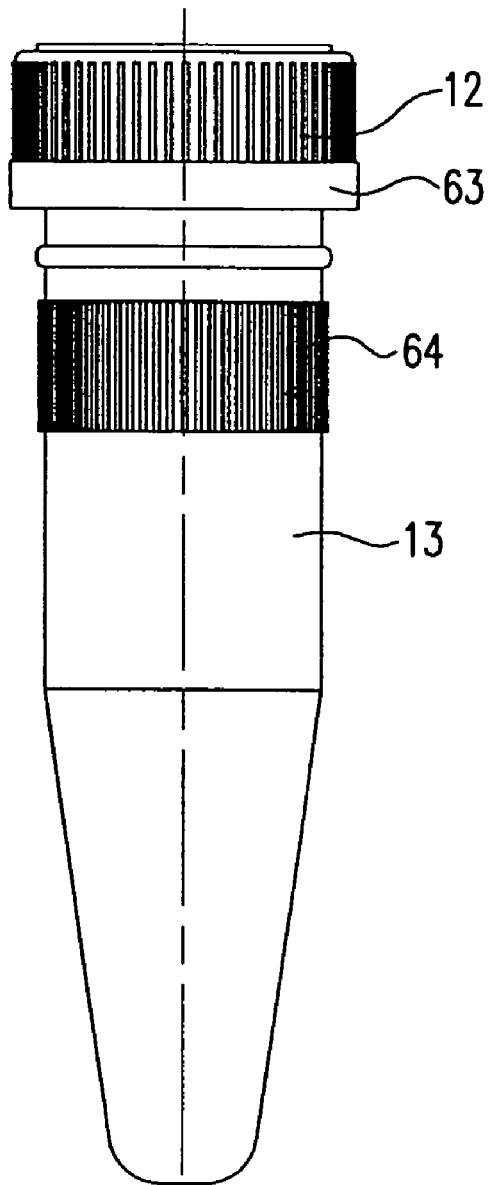
FIG. 6a shows the reaction vessel with lid in a side view.
Figure 6B:
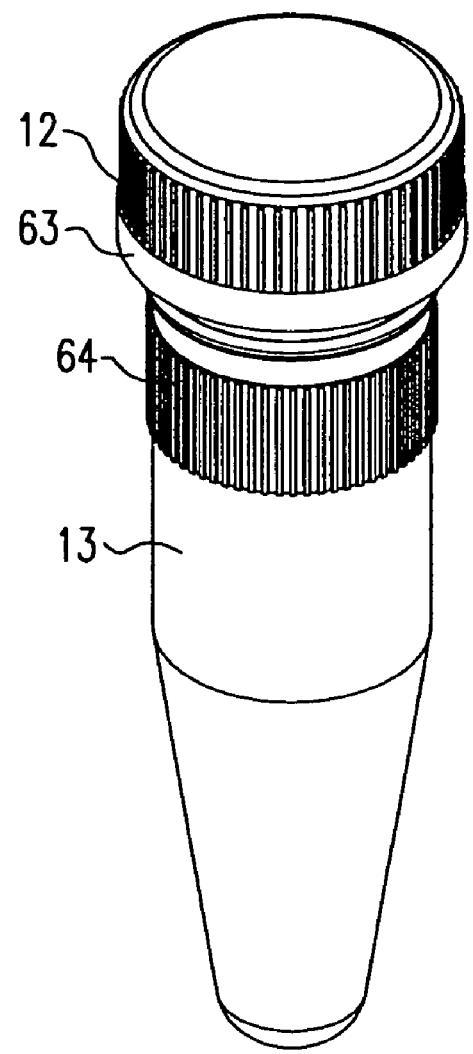

Formed on each of the gripping surfaces 25 is at least one vertically-running cutting web 28. In the present embodiment, each gripping surface 25 is provided with one cutting web 28. In the context of the invention, however, it would also be possible to provide several cutting webs on each gripping surface. The height by which the cutting webs 28 project above the gripping surface 25 is less than the wall thickness of a reaction vessel 13 (FIGS. 6a, 6b). In the present embodiment this height is 0.5 mm. From the gripping surface 25, each cutting web 28 tapers to a point, thus forming a vertical cutting edge.

The device according to the invention is suitable for the handling of reaction vessels of the type "microtube 1.5 ml"

provided by the company Sarstedt and distributed under item numbers SAR-72692 and SAR-62692005, respectively (www.scimart.com/tubes/screwcap.html).

Emerging at the upper surface of the framework 18 is a centrally located blind bore 29. Via the blind bore 29, the gripper 11 is pushed on to a rotatably driven pin of the rotating mechanism 10, where it is fixed to the rotating mechanism 10 by means of two locating screws 30.

In the original state, the gripping jaws 20 define with their gripping surfaces 25 an area which is slightly smaller than the circumferential area of a lid 12 which is to be gripped. The area bounded by the lower edges of the insertion slopes 27 is somewhat larger than the circumferential area of a lid 12. Therefore, if the gripper 11 is pushed on to a lid 12, the lid is slightly elastically deformed, and inserted into the area between the gripping jaws 20, until it rests against the stop webs 26. Through the frictional contact between the gripping surfaces 25 and the lid outer wall, the lid is held by the gripper 11, so that it can be handled. In addition, the cutting webs 28 press the lid outer wall slightly inwards, generating form closure so that the gripper 11 is able to exert considerable torque on the lid 12.

Figure 3B:
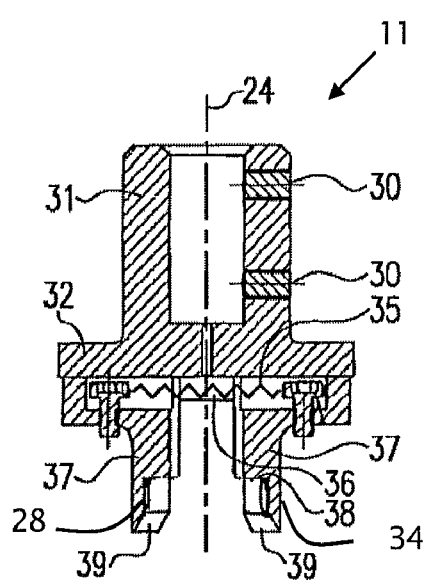
FIG. 3b shows the gripper of FIG. 3a in a sectional view.
Figure 3A:
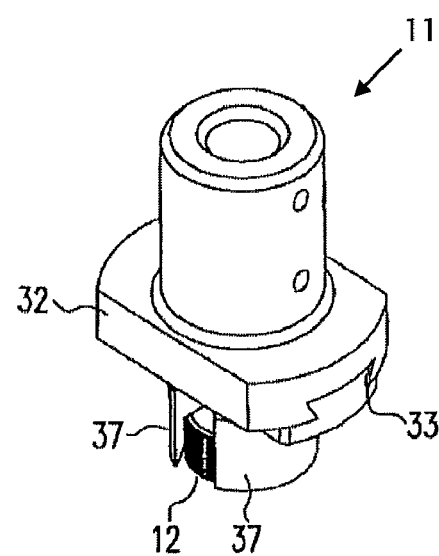
FIG. 3a shows another gripper according to the invention in a perspective view.

FIGS. 3a and 3b show a second embodiment of the gripper 11 according to the invention. In the upper part, this gripper 11 has a tubular section 31, which is provided with two tapped holes for the insertion of locating screws 30, to fix the gripper 11 to a rotatable driven pin of the rotating mechanism 10. Formed at the lower end of the tubular section 31 is a horizontal rail section 32. Formed on the underside of this rail section 32 is a dovetailed slot 33.

Resting and able to slide in the dovetailed slot 33 are two gripping jaws 34, so connected by means of a spring element 35 that the gripping jaws 34 are preloaded in the direction of the axis of symmetry 24. Provided in the area between the two gripping jaws 34 is a spacer element 36, with which the gripping jaws 34 make contact in the original state, i.e. without a lid, owing to the preload of the spring element 35.

The gripping jaws 34 each have a circular-segment-shaped body, in which the centre point of the circular segment lies in the vicinity of the axis of symmetry 24. In the lower third of the gripping jaws 34, a section is milled out of the inner face, so that the gripping jaws 34 have in this area a gripping surface 37 facing towards the axis of symmetry 24 and bounded at the top by a stop step 38. Adjoining the lower edge area of the gripping surfaces 37 in each case is an insertion slope 39 which runs downwards and radially outwards.

Formed on each of the gripping surfaces 37 is a vertical cutting web 28. In the present embodiment, three cutting webs are provided on each gripping surface 37. The design of the cutting webs corresponds to that of the first embodiment of the gripper 11.

In the original state, the two gripping jaws 34 bound with their gripping surfaces 37 an area which is somewhat smaller than the circumferential area of a lid 12 which is to be gripped. The area bounded by the lower edges of the insertion slopes 39 is somewhat larger than the circumferential area of a lid 12. If, therefore, the gripper 11 is pushed on to a lid 12, then the gripping jaws 34 are pushed apart against the spring action of the spring element 35 by the insertion of the lid 12 at the insertion slopes 39, and the lid is inserted into the area between the gripping jaws 34 until it makes contact with the stop steps 38. The lid 12 is held by the gripper 11, through frictional contact between the gripping surfaces 37 and the lid outer wall, so that it may be handled. The cutting webs 28 in turn generate form closure for the transmission of a considerable torque.

Figure 4A:
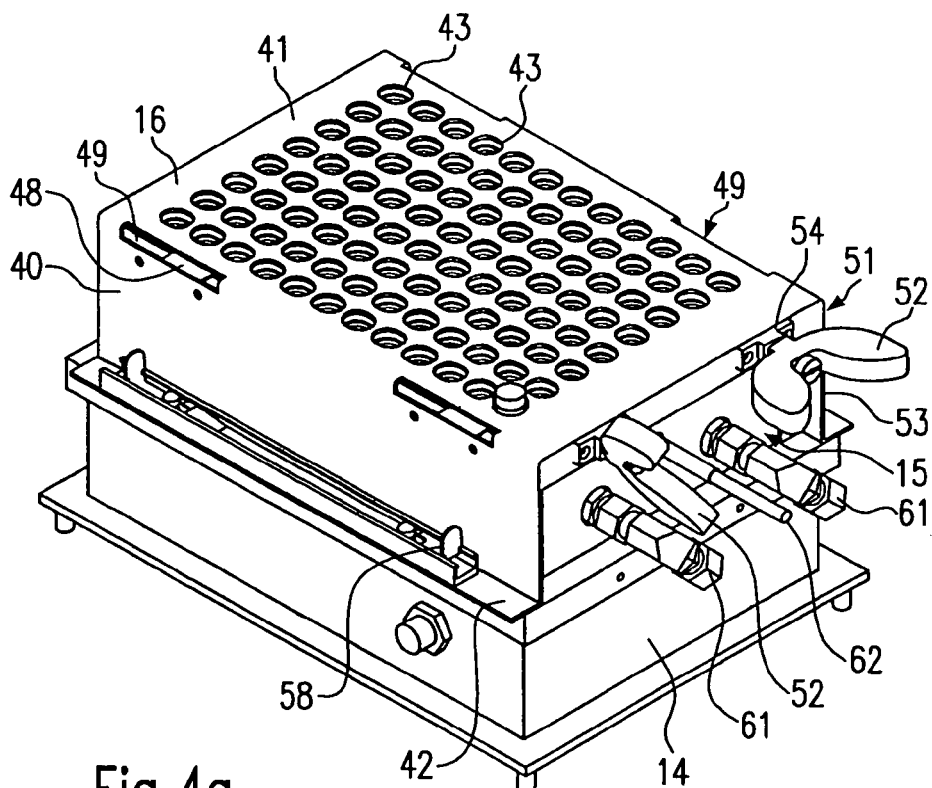
FIG. 4a illustrates a rack according to the invention for holding reaction vessels, together with a thermal block and a vibrator.
Figure 4B:
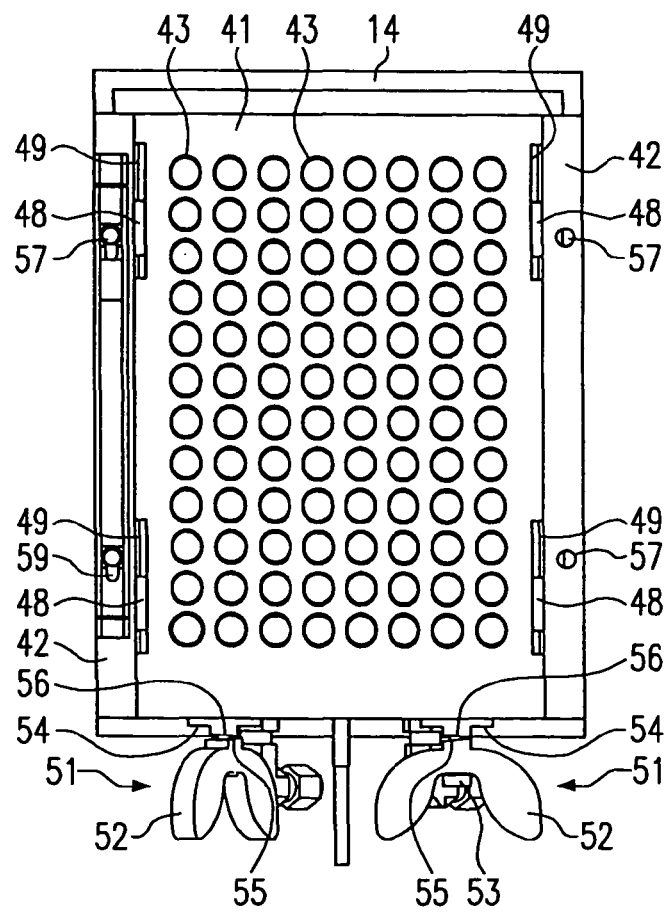
Figure 4C:
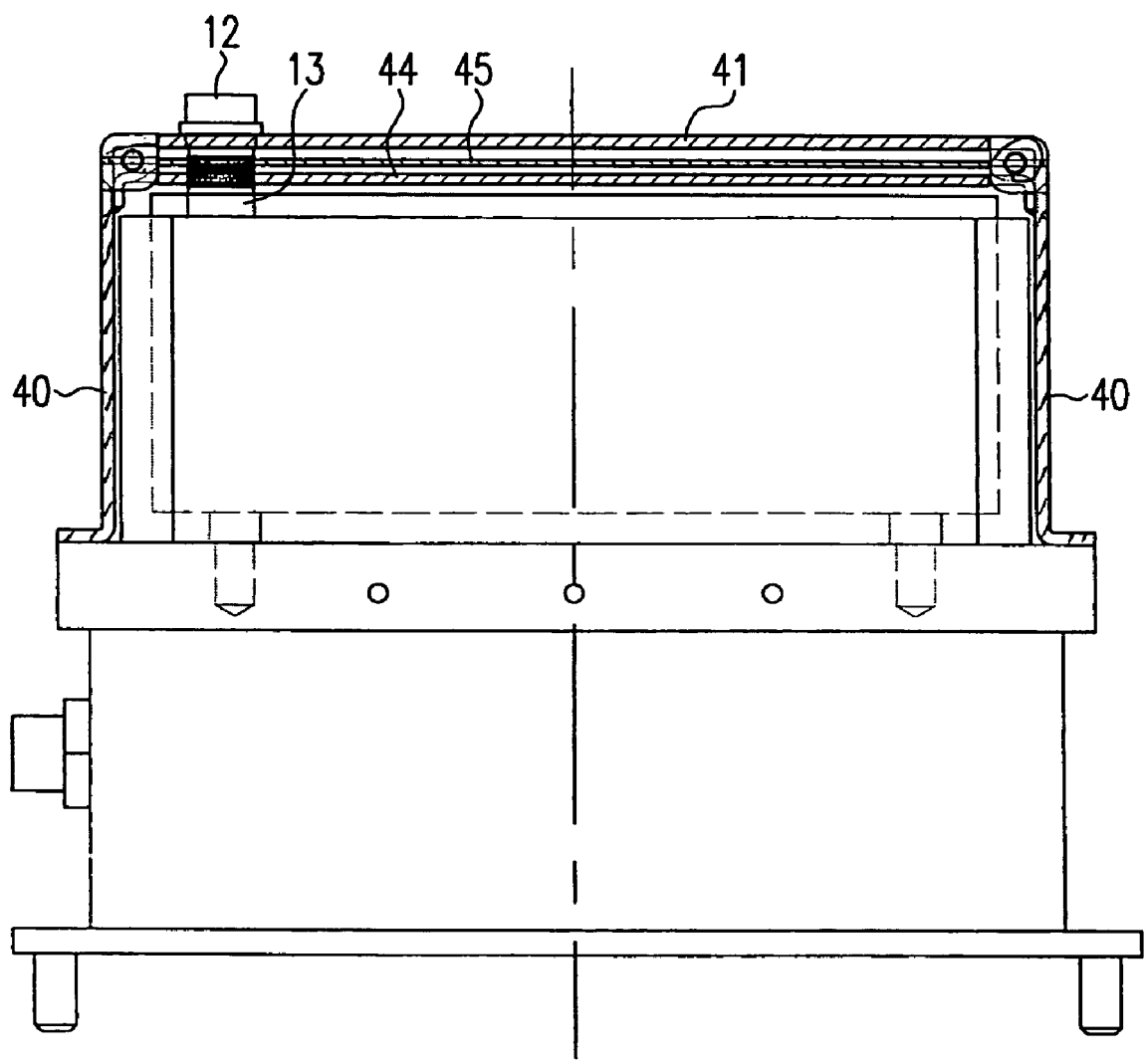

The rack 16 for holding the reaction vessels is explained in detail below (FIGS. 4a, 4b, 4c). This rack 16 is made in a reverse U-shape with two side walls 40 and top 41. The side walls are each curved outwards, thus forming a narrow, strip-shaped base section 42 projecting outwards. The top 41 is in the form of a perforated plate, with openings 43 to hold the reaction vessels inserted in a regular pattern. Beneath the top 41, at a predetermined distance, for example 5 to 10 mm, is another perforated plate, subsequently described as the bottom perforated plate 44. The edge areas of the bottom perforated plate 44 adjoining the side walls 40 are flanged downwards, and the flanged sections are fastened to the side walls 40 for example by soldering or by means of screw connections. The top 41, subsequently described as the top perforated plate 41, and the bottom perforated plate 44 thus define an intermediate space in which a further perforated plate 45 is fitted, hereafter described as the middle perforated plate.

Figure 5A:
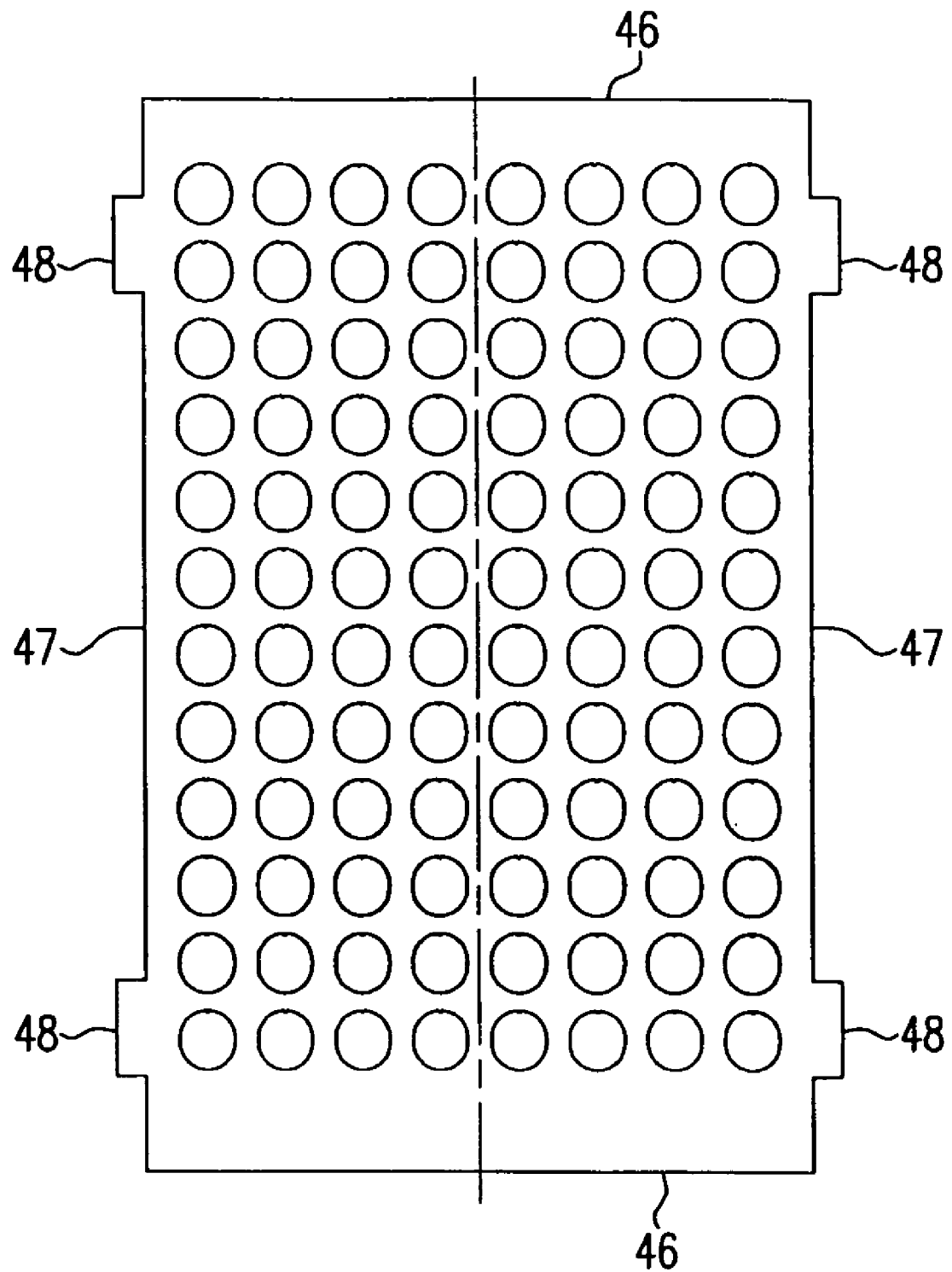
FIG. 5a shows a perforated plate of the rack of FIG. 4a in a top view.

The perforated plate 45 is shown in a top view in FIG. 5a. In a top view this perforated plate is substantially rectangular, with two end edges 46 and two longitudinal edges 47. Moulded on to each of the two longitudinal edges 47 are two lugs 48. The lugs 48 engage in corresponding slits 49 in the side walls 40 (FIG. 4a). The slits 49 are longer than the lugs 48, so that the middle perforated plate 45 is mounted slidably in the direction of its longitudinal edge 47, which defines a direction of sliding.

The middle perforated plate 45 also has openings 43, which have substantially the same shape, size and pattern as the openings 43 of the top and bottom perforated plates 41, 44.

The openings of the top and bottom perforated plates 41, 44 are arranged, in a straight-line projection, exactly above one another. The middle perforated plate 45 may be shifted into a first position in which the openings of all three perforated plates are arranged exactly one above the other, i.e. the corresponding openings of the three perforated plates are aligned with one another. The middle perforated plate 45 may be shifted into a second position in which its openings are offset relative to the openings of the top and bottom perforated plates 41, 44, so that the openings are no longer in alignment with one another.

Figure 5B:
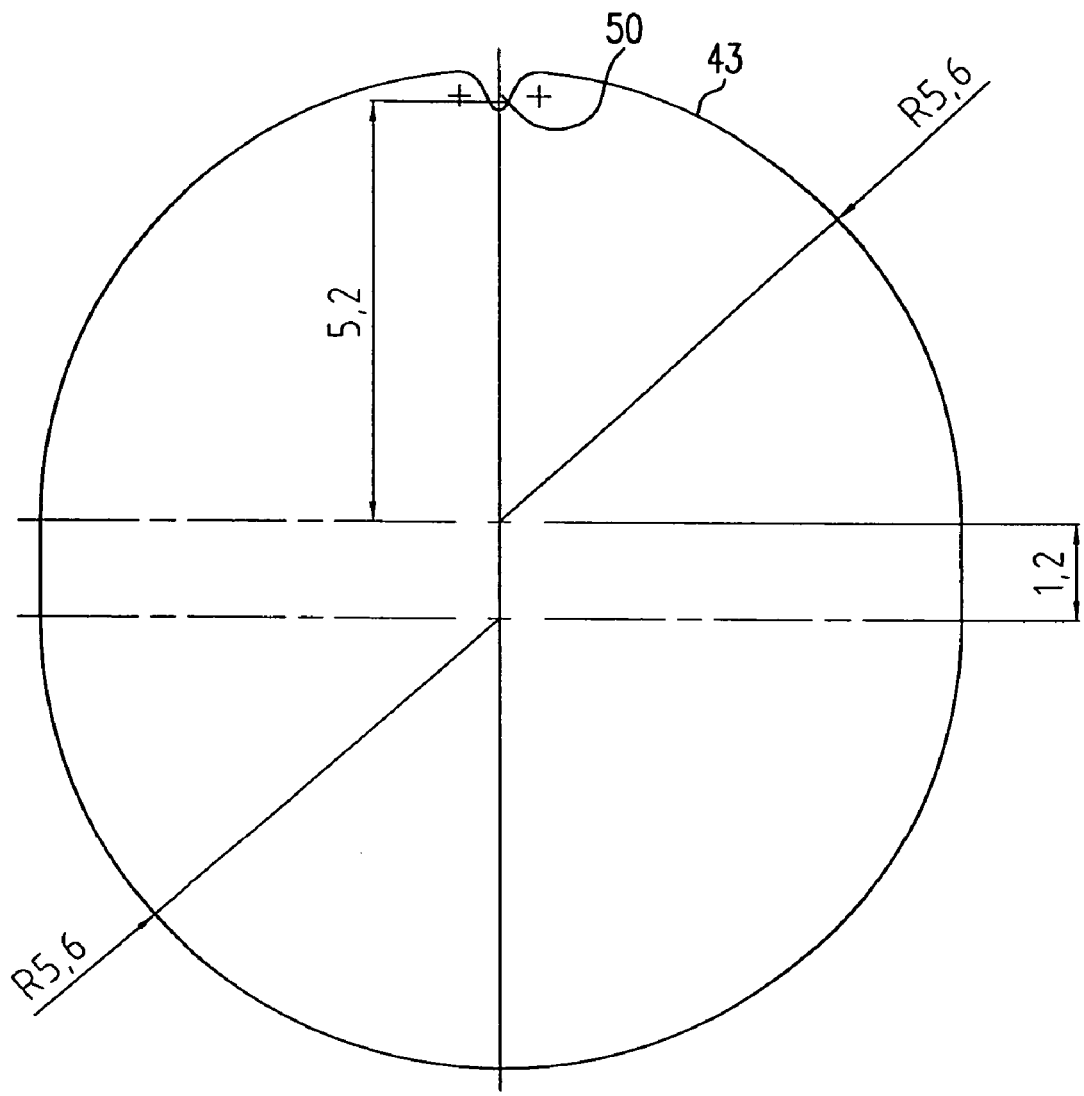
FIG. 5b shows an enlarged view of an opening of the perforated plate.

The openings 43 (FIG. 5b) are somewhat extended in the direction of displacement, and have the shape of two semicircular segments, a short distance apart from one another. In the present embodiment, the semicircular segments have a radius of 5.6 mm and are shifted 1.2 mm apart. At the apex of one of the two semicircular segments, a small projection 50 is made in the area of the opening. This projection is thus located in the area of intersection between a centre line of the opening 43 running in the direction of displacement, and the boundary edge of the opening. Viewed from above, the projections 50 have only roundings and no corners, so that they do not perforate the reaction vessels.

The openings of all three perforated plates 41, 44, 45 have corresponding projections 50, with the projections of the top and bottom perforated plates 41, 44 being arranged in each case diametrically opposite the projections of the middle perforated plate.

Located on the end face of the rack 16 are two adjusting devices 51, by means of which the middle perforated plate may be moved to and fro in the direction of displacement between the first and second positions, and can also be fixed in the second position. Each adjusting device 51 has a wing screw 52. The wing screws 52 have a central hole, in which rests a rod connected to the middle perforated plate 45. In the longitudinal direction, this rod has a tapped hole, into which is screwed a screw 53 which rests with its screw head on the wing screws 52. On the side facing the perforated plates, the wing screws each fit up against a corresponding stop element 54, which is firmly connected to the top and bottom perforated plates 41, 44. The rod connected to the middle perforated plate reaches through each of the stop elements 54. The stop elements 54 and the wing screws 52 each have a contact surface 55, 56.

The surfaces 55, 56 are arranged at an acute angle to a plane located at right-angles to the direction of movement. Provided between the stop elements 54 and the middle perforated plate 45 is a spring element (not illustrated), which presses the perforated plate 45 away from the stop elements 54. If the wing screws 52 lie with their contact surfaces 55 flat against the contact surfaces 56 of the stop elements 54, then the middle perforated plate is positioned the maximum distance away from the stop elements 54. By means of the screws 53 this position is set so that here the openings 43 of the middle perforated plate 45 are aligned flush with the openings 43 of the top and bottom perforated plates 41, 44. If now the wing screws 52 are turned through 180°, then the angled contact surfaces effect a displacement of the wing screws 52 relative to the stop elements 54. As a result of this, the middle perforated plate 45 is moved against the spring effect of the spring element towards the stop elements 54, and assumes its second position in which its openings 43 are offset relative to the openings of the top and bottom perforated plates 41, 44. The contact surfaces 55, 56 are provided with a small snap-in recess and a corresponding snap-in projection, so that the wing screws engage in the stop elements 54 when the middle perforated plate is in its second position.

Made in each of the two base sections 42 are four holes 57. Provided in each case on one of the two base sections, in the area immediately above the holes 57, is a slide 58. Each slide 58 has an elongated hole, which is enlarged at one end to match the holes 57. Provided on the vibrator station 14 are corresponding pins, each with a head 60 passing through the holes 57. When the rack 16 is placed on the vibrator station 14, the heads 60 are guided through the holes 57 and the enlarged area of the elongated holes 59. The slides 58 are then moved in such a way that the narrower area of the elongated holes 59 engages the heads 60 from behind and the rack is fixed on to the vibrator station 14. Suitable hook-shaped elements, formed on the vibrator station 14, reach through the holes 57 of the other base section 42. By this means the rack 16 is fixed to the vibrator station 14 in such a way that it is held securely to the vibrator station even during the vibratory movements executed by the vibrator station.

In the embodiment shown in FIGS. 4a and 4b, connections 61 for the hoses 17 are provided on the end face of the thermal block 15. In the area between the connections 61 is an electrical lead 62 to a temperature sensor fitted to the thermal block 15.

The rack 16 according to the invention permits the preparation of a series of specimens outside the robot 1, with scope for arranging on and fixing to the rack 16 a multiplicity of reaction vessels. Here the middle perforated plate is in its first position, in which its openings coincide with the openings of the top and bottom perforated plate. The reaction vessels are then inserted for example by hand in the openings 43. The openings are so dimensioned that the reaction vessels 13 can not fall through them, but instead lie on the top of the top perforated plate 41 with an annular web 63 formed on the reaction vessels 13. When all the reaction vessels 13 are arranged in the rack 16, the middle perforated plate 45 is brought into its second position by turning the wing screws 52. This clamps the reaction vessels 13 firmly in the rack due to the displacement of the openings 43 of the middle perforated plate relative to the corresponding openings 43 of the top and bottom perforated plates. In particular, the projections 50 press somewhat into the elastically yielding plastic material of the reaction vessels 13 so that, in addition to the clamping frictional contact, form closure is also obtained between the rack 16 and the reaction vessels 13. The middle and bottom perforated plates 45, 44 are preferably so arranged on the rack 16 that they act on a section 64 of the reaction vessels 13 on which continuous vertical ribs are formed.

The rack 16, loaded in this way, may easily be handled and fixed on to the vibrator station 14. It is also possible for the loaded rack to be fed to other process steps, e.g. autoclaving.

The rack according to the invention fixes a multiplicity of reaction vessels non-rotatably in a vertical direction. Because of this, the rack according to the invention may be used very advantageously in conjunction with the gripper according to the invention, since the high forces exerted when the gripper is pushed on to a lid on a reaction vessel and when a gripper is removed from a lid screwed to a reaction vessel, may be absorbed safely and without creating problems in use of the rack.

The rack according to the invention is moreover very simple in design and may therefore be manufactured cost-effectively. A further advantage lies in the fact that conventional reaction vessels with screw lids may be used.

The invention is explained above with the aid of an embodiment. In the context of the invention it is also possible that, instead of the three adjusting screws 23 of the gripper 11 according to the first embodiment, the base area of the blind bore 29 is provided with a conical taper, and that the upper part of the gripping jaws are in contact with this conical surface. The taper is located on a threaded tree rod resting in a vertical tapped hole in the gripper. By turning the threaded tree rod, the vertical position of the taper is changed and the gripping jaws are swivelled around the shafts 21 so that the holding area is adjusted.

According to a further modification of the invention, quick-action clamping elements, such as are known from bicycle hubs, may be used instead of the adjusting devices 51 described above.

Within the scope of the invention it is also possible for the robot to have several robot arms running on a common horizontal rail.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes

What is claimed is:

1. A device for the opening and closing of one or more reaction vessels, comprising:
a holding device capable of non-rotatable holding of the one or more reaction vessels, wherein the holding device has a clamping mechanism to clamp and hold the one or more reaction vessels, the holding device comprising:
three perforated plates arranged one above the other as a bottom plate, a middle plate and a top plate, each of the perforated plates having a plurality of openings to hold the one or more reaction vessels, the top plate and the bottom plate being fixed in a stationary position with the openings in the top plate directly aligned with the openings in the bottom plate, the middle plate being capable of sliding in a longitudinal direction between a first position in which the openings in the middle plate are aligned with the openings of the top plate and the bottom plate, and a second position in which the openings in the middle plate are arranged offset relative to the openings of the top plate and bottom plate, whereby when the middle plate is in the first position the one or more reaction vessels can be inserted into or removed from the openings of the perforated plates, and when the middle plate is in the second position the middle plate presses and immobilizes the one or more reaction vessels in the holding device, and a means for moving and fixing the middle plate in the second position;

a gripper capable of gripping a lid of one of the reaction vessels, the gripper comprising:

a blind bore, and at least two gripping jaws comprising a gripping surface with one or more vertically running cutting webs effective to hold the lid, wherein the gripping jaws are arranged so that the lid is inserted between the gripping jaws, and the lid is held by the gripping jaws through frictional contact while the lid is lifted off the reaction vessel; and a handling arm comprising at one end a rotating mechanism comprising a rotatably driven pin that is fixed in the blind bore of the gripper and rotates the gripper with the inserted lid clockwise/counterclockwise with respect to the longitudinal axis the reaction vessels.

2. The device according to claim 1, wherein the gripping jaws comprise insertion slopes running downwards and radially outwards from lower edges of the gripping surfaces.

3. The device according to claim 1, wherein the height by which the one or more cutting webs project beyond the gripping surface is 0.5 mm.

4. The device according to claim 1, wherein the middle plate contains a plurality of projections each extending into the interior of each of the plurality of openings, each projection being located at an edge of the opening at the intersection of the central axis of the opening and the boundary edge of the opening at the longitudinal direction of sliding.

5. The device according to claim 4, wherein the top plate and/or the bottom plate contains a plurality of projections each extending into the interior of each of the plurality of openings, each projection being arranged opposite the projection of the corresponding opening of the middle plate.

* * * * *